(12) United States Patent
Curtis et al.

(10) Patent No.: US 6,613,766 B1
(45) Date of Patent: Sep. 2, 2003

(54) PENTAAZA-CYCLOPENTAL[A] NAPHTHALENE DERIVATIVES AS LIGANDS FOR $GABA_A$ $\alpha 5$ RECEPTORS

(75) Inventors: Neil Roy Curtis, Buntingford (GB); Janusz Jozef Kulagowski, Sawbridgeworth (GB); Francine Sternfeld, London (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/831,547

(22) PCT Filed: Nov. 3, 1999

(86) PCT No.: PCT/GB99/03636

§ 371 (c)(1),
(2), (4) Date: May 10, 2001

(87) PCT Pub. No.: WO00/29412

PCT Pub. Date: May 25, 2000

(30) Foreign Application Priority Data

Nov. 12, 1998 (GB) ................................................ 9824897

(51) Int. Cl.[7] .......................... A61K 31/50; A61P 25/08; C07D 487/00
(52) U.S. Cl. ....................................... 514/248; 544/234
(58) Field of Search ............................ 514/248; 544/234

(56) References Cited

U.S. PATENT DOCUMENTS

| | | | |
|---|---|---|---|
| 5,145,684 A | 9/1992 | Liversidge et al. | 424/489 |
| 6,255,305 B1 * | 7/2001 | Broughton et al. | 514/228.5 |

FOREIGN PATENT DOCUMENTS

| | | |
|---|---|---|
| EP | 085840 | 1/1983 |
| EP | 134946 | 6/1984 |
| WO | WO 96/25948 | 8/1996 |
| WO | WO 98/04559 | 2/1998 |
| WO | WO 98/04560 | 2/1998 |
| WO | WO 98/50385 | 11/1998 |
| WO | WO 99/06407 | 2/1999 |

OTHER PUBLICATIONS

R. K. McNamara et al., Psychobiology, 21:101–108(1993).

* cited by examiner

Primary Examiner—Richard L. Raymond
Assistant Examiner—Tamthom N. Truong
(74) Attorney, Agent, or Firm—J. Eric Thies; Melvin Winokur

(57) ABSTRACT

A class of 1,2,3a,4,x-pentaaza-cyclopenta[a]naphthalene compounds (x=6, 7, 8 or 9) is described. The compounds have a high affinity for the $GABA_A$ $\alpha 5$ receptors and show inverse agonist activity thereat. The compounds are useful in therapy where cognition enhancement is required.

10 Claims, No Drawings

PENTAAZA-CYCLOPENTAL[A] NAPHTHALENE DERIVATIVES AS LIGANDS FOR GABA$_A$ α5 RECEPTORS

This is a 371 application of PCT/GB99/03636 and claims benefit from British Application No. 9824897.4, filed Nov. 12, 1998.

The present invention relates to a class of substituted pentaaza-cyclopenta[a]naphthalene derivatives and to their use in therapy. More particularly, this invention is concerned with substituted 1,2,3a,4,x-pentaaza-cyclopenta[a]naphthalene derivatives which are ligands for GABA$_A$ receptors containing the α5 subunit and are therefore useful in the therapy where cognition enhancement is required.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native GABA$_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of GABA$_A$ receptors in the rat. Subtype assemblies containing α2 and α3 subunits respectively account for about 25% and 17% of GABA$_A$ receptors in the rat. Subtype assemblies containing an α5 subunit are primarily hippocampal and represent about 4% of receptors in the rat.

A characteristic property of some GABA$_A$ receptors is the presence of a number of modulatory sites, of which the most explored is the benzodiazepine (BZ) binding site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the α1 subunit in combination with β2 and γ2. This is the most abundant GABA$_A$ receptor subtype, representing almost half of all GABA$_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist γ-CCM enhanced spatial learning in the Morris watermaze. However, γ-CCM and other conventional benzodiazepine receptor inverse agonists are proconvulsant or convulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

The present invention provides a compound of the formula I:

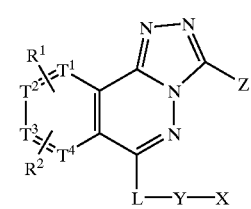

wherein:

R$^1$ is hydrogen, halogen or CN or a group CF$_3$, OCF$_3$, C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;

R$^2$ is hydrogen, halogen or CN or a group CF$_3$, OCF$_3$, C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy each of which groups is unsubstituted or substituted with one or two halogen atoms;

L is O, S or NR$^n$ where R$^n$ is H, C$_{1-6}$alkyl or C$_{3-6}$cycloalkyl;

one of T$^1$, T$^2$, T$^3$ and T$^4$ is nitrogen or N$^+$—O$^-$ and the others are CH;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OCOR^3$, $NR^4R^5$, $NR^4COR^5$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4COR^5$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with the nitrogen atom to which they are attached, form a 4–7 membered heteroaliphatic ring containing the nitrogen atom as the sole heteroatom, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{2-4}$alkylene or $C_{1-4}$alkylidene optionally substituted by an oxo group or Y is a group $(CH_2)_jO$ wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

In a particular embodiment of the invention, one of $T^1$, $T^2$, $T^3$ and $T^4$ is nitrogen and the others are CH, and Y is optionally branched $C_{1-4}$alkylidene optionally substituted by an oxo group or Y is a group $(CH_2)_jO$ wherein the oxygen atom is nearest the group X and j is 2, 3 or 4.

The compound is generally in the form of the free base.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

As used herein, the expression "$C_{1-4}$alkylidene" refers to alkanediyl groups having the free valancies on the same carbon atom, while the expression. "$C_{2-4}$alkylene" refers to alkanediyl groups having the free valencies on different carbon atoms.

The expression "$C_{3-6}$cycloalkyl" as used herein includes cyclic propyl, butyl, pentyl and hexyl groups such as cyclopropyl and cyclohexyl.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

$R^1$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstitutecd or independently substituted by one or two halogen atoms or nitro, cyano, amino, methyl or $CF_3$ groups. $R^1$ is typically hydrogen, fluorine, chlorine, bromine or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or by a pyridyl or phenyl ring each of which rings may be unsubstituted or substituted by one or two halogen atoms or nitro, cyano, amino, methyl or $CF_3$ groups and is generally hydrogen, fluorine or pyridylmethoxy, typically hydrogen.

$R^2$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms. $R^2$ is typically hydrogen, fluorine, chlorine or bromine, and is generally hydrogen or fluorine, typically hydrogen.

Preferably L is an oxygen atom. L may also be $NR''$ in which $R''$ is preferably hydrogen or methyl. $R''$ may be hydrogen.

X is generally: pyridyl, pyrazinyl, pyridazinyl or pyrimidinyl optionally substituted by a halogen atom or a group and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or which is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms. In particular X is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X is optionally fused to a benzene ring, or X is pyrazolyl, isothiazolyl, isoxazolyl, 1,2,4-triazolyl, thiazolyl, 1,2,3-triazolyl or imidazolyl which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$, or X is phenyl which is unsubstituted or substituted by chlorine. Specific values of X are 2-pyridyl, 6-methylpyridin-2-yl, 3-pyridyl, 4-pyridyl, 3,5-dimethylpyrazol-1-yl, 3-methoxypyridin-2-yl, 3-methylisoxazol-5-yl, pyrazol-1-yl, 6-chloropyridin-2-yl, 6-bromopyridin-2-yl, 6-methoxypyridin-2-yl, 6-isopropoxypyridin-2-yl, 6-N,N-dimethylpyridin-2-yl, 6-(imidazol-1-yl)pyridin-2-yl, 3-pyridazino, 4-pyrimidinyl, pyrazin-2-yl, 2-quinolinyl, 2-quinoxalyl, 2-(4-trifluoromethyl)pyridyloxy, 4-methylisothiazolyl, 2,6-dichlorophenyl, 4-methylthiazol-5-yl, 2-methylthiazol-4-yl, 2-[1-(3-trifluoromethyl)pyrid-6-yl]imidazolyl, 1-benzylimidazol-2-yl, 1-(4-chlorophenyl)-1,2,3-triazol-4-yl, 3-chloro-2-methyl-5-trifluoromethylpyrazol-4-yl, 1-methyl-1,2,4-triazol-3-yl, (5-trifluoromethyl)pyridyl-2-yl, (3-trifluoromethyl)pyrid-2-yl, (4-trifluoromethyl)pyrid-2-yl, 1-methylimidazol-2-yl, 2-{[2-(trimethylsilyl)ethoxy]methyl}-1,2,4-triazol-3-yl, 3-methylimidazol-4-yl, 1,2,4-triazol-3-yl, 1-isopropyl-1,2,4-triazol-3-yl, 4-methyl-1,2,4-triazol-3-yl, 1,2,3-triazol-4-yl, isothiazol-3-yl, 1-ethyl-1,2,4-triazol-3-yl, 2-methyl-1,2,3-triazol-4-yl, 1-methyl-1,2,3-triazol-4-yl, 2-methyl-1,2,4-triazol-3-yl, 1-methylimidazol-4-yl, 5-tert-butylpyridazin-3-yl and 1-methyl-1,2,3-triazol-5-yl. Still further particular values of X are 2-benzyl-1,2,4-triazol-3-yl, 1-benzyl-1,2,4-triazol-3-yl, 1-nbutyl-1,2,4-triazol-3-yl, 2-ethyl-1,2,4-triazol-3-yl, 2-methylpyrazol-3-yl, 1-methylpyrazol-3-yl, 1-npropyl-1,2,4-triazol-3-yl, 1-(2,2,2-trifluorethyl)-1,2,4-triazol-3-yl, 1-ethyl-1,2,3-triazol-5-yl, 1-methyltetrazol-2-yl, imidazol-2-yl, 2-npropyl-1,2,4-triazol-3-yl, 1-ethyl-1,2,3-triazol-4-yl, 2-ethyl-1,2,3-triazol-4-yl, 1-ethylimidazol-5-yl, 1-ethylimidazol-4-yl, 1-npropyl-1,2,4-triazol-3-yl and 1-ethyl-1,2,3-triazol-5-yl. In particular X is pyrid-2-yl, 2-methyl-1,2,4-triazol-3-yl, 1-methyl-1,2,4-triazol-3-yl, 1-methyl-1,2,3-triazol-4-yl, 3-methyl-1,2,3-triazol-4-yl or 2-ethyl-1,2,4-triazol-3-yl.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent. In particular X is optionally substituted pyridine. The optional substituents are generally $CF_3$, halogen or $C_{1-6}$alkyl, particularly methyl or ethyl, especially methyl. When X is pyridine it may be in the form of the N-oxide.

When X is a substituted 5-membered heteroaromatic ring: $R^x$ is preferably halogen, $R^3$ or a pyridyl, phenyl or benzyl ring which ring is optionally independently substituted by one, two or three halogen atoms or $C_{1-6}$alkyl or $CF_3$ groups and more preferably $R^x$ is methyl, $CF_3$, chlorine or a phenyl, pyridyl or benzyl ring which ring is unsubstituted or substituted by chlorine or $CF_3$; and $R^y$ and $R^z$ are preferably halogen or $R^3$, and more preferably methyl, $CF_3$ or chlorine. X is especially an optionally substituted triazole, either a 1,2,3- or 1,2,4-triazole, which is preferably substituted by methyl or ethyl, especially methyl.

Particularly aptly X is an unsubstituted six-membered heteroaromatic group containing one or two nitrogen atoms.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is CH2 or $CH_2CH_2$ and most preferably $CH_2$.

$R^v$ is suitably chlorine, $R^6$, thienyl, furyl, pyridyl or $NR^7R^8$, more particularly $R^6$, thienyl, furyl, pyridyl or $NR^7R^8$, for example $C_{1-6}$alkyl, $C_{3-6}$cycloalkyl, hydroxyC$_{1-6}$alkyl, pyridyl, thienyl or amino and more particularly methyl, ethyl, ethoxy, isopropyl, cyclopropyl, thienyl or pyridyl, and even more particularly methyl, ethyl, isopropyl, cyclopropyl, thienyl or pyridyl. A further example of $R^v$ is chlorine.

$R^w$ is suitably $R^6$, for example $C_{1-6}$alkyl, $CH_2F$ or hydroxyC$_{1-6}$alkyl, more particularly methyl, $CH_2F$ or hydroxymethyl. Generally $R^w$ is absent.

$R^x$ may be halogen, $R^3$, $OR^3$, $OCOR^3$, $NR^4R^5$, $NR^4COR^5$, CN or $R^9$.

Z is preferably a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$, is $R^6$ or CN.

Suitable values for Z include pyrimidinyl, pyrazinyl, pyrrolyl, oxazolyl, isoxazolyl, thiazolyl, isothiazolyl, oxadiazolyl and thiadiazolyl groups which groups are optionally substituted by $R^6$, thienyl, furyl, pyridyl or $NR^7R^8$ groups.

Z is very aptly a 5-membered heteroaromatic ring containing one oxygen and one or two nitrogen ring atoms and is optionally substituted by, a group $R^6$. In such compounds $R^3$ is favourably a methyl group.

Favoured values for Z include optionally substituted isoxazoles and oxadiazoles.

Z may be unsubstituted.

Z may very aptly be substituted by methyl.

Z is especially isoxazole which is unsubstituted or substituted by $C_{1-6}$alkyl or $C_{1-6}$alkoxy, especially methyl or ethoxy.

Particular values of Z are 3-methyloxadiazol-5-yl, 3-cyclopropyloxadiazol-5-yl, 5-methylisoxazol-3-yl, 5-(3-pyridyl)-isoxazol-3-yl, 5-hydroxymethylisoxazol-3-yl, 4,5-dimethylisoxazol-3-yl, 5-ethylisoxazol-3-yl, 5-cyclopropylisoxazol-3-yl, 5-isopropylisoxazol-3-yl, isoxazol-3-yl, 5-thienylisoxazol-3-yl, 5-fluoromethylisoxazol-3-yl, 4-methylisoxazol-3-yl, 5-ethoxylsoxazol-3-yl, 4-methyl-5-chloroisoxazol-3-yl, 5-trifluoromethylisoxazol-3-yl, 5-(pyrid-2-yl)isoxazol-3-yl, 5-benzylisoxazol-3-yl, 5-chloroisoxazol-3-yl, 3-cyclopropyloxadiazol-5-yl, 5-methoxylsoxazol-3-yl, 5-methoxymethylisoxazol-3-yl, 5-methyloxadiazol-3-yl, pyrazin-2-yl and 3-methylisoxazol-5-yl. In particular Z is 5-methylisoxazol-3-yl, isoxazol-3-yl or 5-ethoxylsoxazol-3-yl.

$R^3$ may be $C_{1-6}$alkyl, $C_{2-6}$alkenyl, $C_{2-6}$alkynyl, $C_{3-6}$cycloalkyl, hydroxy$C_{1-6}$alkyl or $CF_3$.

Generally $R^3$ is $C_{1-6}$alkyl, $C_{2-6}$alkoxy or $CF_3$. In particular $R^3$ is methyl, methoxy, ispropoxy or trifluoromethyl.

Generally $R^4$ and $R^5$ are independently hydrogen or $C_{1-6}$alkyl, in particular hydrogen or methyl, for example both can be methyl.

$R^6$ may be $C_{1-6}$alkyl, $C_{2-6}$alkenyl, $C_{2-6}$alkynyl, $C_{3-6}$Cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$. Generally $R^6$ is $CH_2F$, $CF_3$, $C_{1-6}$alkyl, $C_{3-6}$cycloalkoxy, $C_{1-6}$alkyl or hydroxy$C_{1-6}$alkyl, for example, $CH_2F$, $CF_3$, methyl, ethyl, iospropyl, cyclopropyl or hydroxymethyl, particularly methyl or cyclopropyl. Alternatively $R^6$ is $C_{1-6}$alkyl or hydroxy$C_{1-6}$alkyl, for example, methyl, ethyl, isipropyl, cyclopropyl or hydroxymethyl.

Generally $R^7$ and $R^8$ are independently hydrogen or $C_{1-6}$alkyl, particularly hydrogen or methyl.

Generally $R^9$ is pyrazolyl, imidazolyl, phenyl, benzyl or pyridyl optionally substituted by halogen, preferably chlorine, or $CF_3$. In particular $R^9$ can be imidazol-1-yl, 3-trifluoromethylpyrid-5-yl, benzyl and 4-chlorophenyl.

Generally $R^{10}$ is $C_{1-6}$alkyl or $CF_3$, in particular methyl or $CF_3$, for example $CF_3$.

One of $T^1$, $T^2$, $T^3$ and $T^4$ represents N or $N^+$—O— while the others represent CH. Thus, the compounds of the invention are 1,2,3a,4,x-pentaaza-cyclopenta[a]naphthalene derivatives, where x is 6, 7, 8 or 9, or the corresponding 6-, 7-, 8-, or 9-N-oxides. Preferably, one of $T^1$, $T^2$, $T^3$ and $T^4$ represents N, most preferably $T^3$ or $T^4$ represents N.

In a preferred subclass of compounds of formula I:

$R^1$ and $R^2$ are hydrogen;

L is O;

X is pyridine or triazole and is unsubstituted or substituted by $C_{1-6}$alkyl or $CF_3$;

Y is $CH_2$; and

Z is isoxazole which is unsubstituted or substituted by $C_{1-6}$alkyl or $C_{1-6}$alkoxy.

In a particular embodiment of this subclass, X is pyridine or triazole and is unsubstituted or substituted by $C_{1-6}$alkyl.

For use in medicine, the salts of the compounds of formula I will be pharmaceutically acceptable salts. Hence in a favoured aspect this invention provides the compounds of the formula I and pharmaceutically acceptable salts thereof. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the present invention.

It will be understood by the skilled person that when a five-membered heterocyclic ring is referred to in the foregoing having four heteroatoms in the ring, then all these heteroatoms are nitrogen. It will further be understood that when a substituted five-membered heterocyclic ring is referred to having two nitrogen atoms and an oxygen or sulphur atom in the ring, then only one substituent may be present so that aromaticity is maintained. Thus, for example, in such a case X may only be substituted by $R^x$ and Z may only be substituted by $R^y$.

Specific compounds within the scope of the present invention include:
3-(5-methylisoxazol-3-yl)-5-(2-pyridylmethyloxy)-1,2,3a,4, 6-pentaaza-cyclopenta[a]naphthalene;
3-(5-methylisoxazol-3-yl)-5-(2-pyridylmethyloxy)-1,2,3a,4, 9-pentaaza-cyclopenta[a]naphthalene;
3-(5-methylisoxazol-3-yl)-5-(2-pyridylmethyloxy)-1,2,3a,4, 7-pentaaza-cyclopenta[a]naphthalene;
3-(5-methylisoxazol-3-yl)-5-(2-pyridylmethyloxy)-1,2,3a,4, 8-pentaaza-cyclopenta[a]naphthalene;
3-(5-methylisoxazol-3-yl)-5-(2-methyl-1,2,4-triazol-3-ylmethyloxy)-1,2,3a,4,6-pentaaza-cyclopenta[a]naphthalene;
3-(5-ethoxylsoxazol-3-yl)-5-(1-methyl-1,2,4-triazol-3-ylmethyloxy)-1,2,3a,4,6-pentaaza-cyclopenta[a]naphthalene;
3-isoxazol-3-yl-5-(2-methyl-1,2,4-triazol-3-ylmethoxy)-1,2,3a,4,6-pentaatza-cyclopenta[a]naphthalene;
3-isoxazol-3-yl-5-(1-methyl-1,2,4-triazol-3-ylmethoxy)-1,2,3a,4,6-pentaaza-cyclopenta[a]naphthalene;
3-(5-methylisoxazol-3-yl)-5-(1-methyl-1,2,4-triazol-3-ylmethoxy)-1,2,3a,4,6-pentaaza-cyclopenta[a]naphthalene;
3-(5-methylisoxazol-3-yl)-5-(1-methyl-1,2,3-triazol-4-ylmethoxy)-1,2,3a,4,6-pentaaza-cyclopenta[a]naphthalene;
3-(5-methylisoxazol-3-yl)-5-(3-methyl-1,2,3-triazol-4-ylmethoxy)-1,2,3a,4,6-pentaaza-cyclopenta[a]naphthalene;
3-(5-methylisoxazol-3-yl)-5-(2-ethyl-1,2,4-triazol-3-ylmethoxy)-1,2,3a,4,6-pentaaza-cyclopenta[a]naphthalene;
3-(5-ethoxylsoxazol-3-yl)-5-(1-methyl-1,2,3-triazol-4-ylmethoxy)-1,2,3a,4,6-pentaaza-cyclopenta[a]naphthalene;
3-(5-ethoxylsoxazol-3-yl)-5-(3-methyl-1,2,3-triazol-4-ylmethoxy)-1,2,3a,4,6-pentaaza-cyclopenta[a]naphthalene;
3-(5-ethoxylsoxazol-3-yl)-5-(2-ethyl-1,2,4-triazol-3-ylmethoxy)-1,2,3a,4,6-pentaaza-cyclopenta[a]naphthalene;
and pharmaceutically acceptable salts thereof.

Further specific compounds within the scope of the invention include:
3-(5-methylisoxazol-3-yl)-5-(2-pyridylmethyloxy)-1,2,3a,4, 7-pentaaza-cyclopenta[a]naphthalene;
3-(5-methylisoxazol-3-yl)-5-(1-methyl-1,2,3-triazol-4-ylmethyloxy)-1,2,3a,4,7-pentaaza-cyclopenta[a]naphthalene;
3-(5-methylisoxazol-3-yl)-5-(1-methyl-1,2,4-triazol-3-ylmethyloxy)-1,2,3a,4,7-pentaaza-cyclopenta[a]naphthalene;

3-(5-methylisoxazol-3-yl)-5-(3-trifluoromethyl-2-pyridylmethyloxy)-1,2,3a,4,7-pentaaza-cyclopenta[a]naphthalene;

3-(5-methylisoxazol-3-yl)-5-(1-methyl-1,2,3-triazol-4-ylmethyloxy)-7-oxide-1,2,3a,4,7-pentaaza-cyclopenta[a]naphthalene;

and pharmaceutically acceptable salts thereof.

Examples of pharmaceutically acceptable salts are hydrochlorides, sulfates, citrates, tartrates, acetates, methanesulfonates, phosphates, oxalates and benzoates.

The compounds of the present invention have a good binding affinity ($K_i$) for the α5 subunit. In a preferred embodiment the compounds of the invention are binding selective for the α5 subunit relative to the α1, 2 and α3 subunits. In another preferred embodiment the compounds are functionally selective for the α5 subunit as partial or full inverse agonists whilst substantially being antagonists at the α1, α2 and α3 subunits.

Cognition enhancement can be shown by testing the compounds in the Morris watermaze as reported by McNamara and Skelton, Psychobiology, 21:101–108. The functional efficacy at the various receptor subtypes can be calculated using the method disclosed in WO-A-9625948.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

Thus, for example, the compounds of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

Those compounds which are not inverse agonists at the α5 subtype may be used as alcohol antagonists or to treat obesity.

The present invention further provides the use of a compound of the present invention in the manufacture of a medicament for the enhancement of cognition, preferably in a human suffering from a dementing illness such as Alzheimer's disease.

Also disclosed.is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For the enhancement of cognition, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

It is preferred that the compounds of the present invention are ground, for example using a pestle and mortar or industrial equivalent thereto, to a particle size of between 1 and 10 μM, and preferably less than 5 μM, before formulation. The compounds may be micronised or sonicised by methods known in the art or nanonised, for example by methods disclosed in U.S. Pat. No. 5,145,684.

The compounds in accordance with the present invention may be prepared by a process which comprises reacting a compound of formula III with a compound of formula IV:

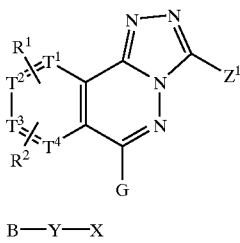

(III)

B—Y—X      (IV)

wherein $T^1$, $T^2$, $T^3$, $T^4$, $R^1$, $R^2$, X and Y are as defined above, G is a leaving group such as chlorine, $OCH_2CF_3$ or tosylate, B is LH where L is as defined above and $Z^1$ is a group Z as defined above or is a moiety which can be converted into a group Z by further reaction.

Compounds of formula III represent a further feature of the present invention. The groups Z which are preferred for compounds of formula I are preferred for these compounds likewise.

The reaction between compounds III and IV when L is O is conveniently effected by stirring the reactants in a suitable solvent, typically N,N-dimethylformamide, in the presence of a strong base such as sodium hydride or lithium bis(trimethylsiiyl)amide, typically without heating and under an inert atmosphere such as nitrogen. When L is NR", the reaction is conveniently effected in the presence of a strong base such as $Et_3N$ or NaH and a solvent such as DMF or DMSO generally for 15 to 60 hours with heating to 50–120° C.

The intermediates of formula III above may be prepared by reacting a compound of formula V, which constitutes a further feature of the present invention, with a compound of formula VI:

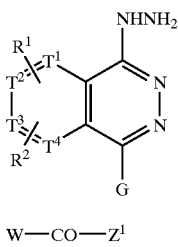

(V)

W—CO—$Z^1$      (VI)

wherein $T^1$, $T^2$, $T^3$, $T^4$, $R^1$, $R^2$, G and $Z^1$ are as defined above, and W represents a suitable leaving group such as $C_{1-6}$alkoxy, chlorine or hydroxy.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from –20° C. to the reflux temperature of the reaction mixture, for a period of time that depends on the reactants employed and the temperature at which the reaction is carried out. The compound of formula VI may be activated by reacting with a compound such as bis (2-oxo-3-oxazolidinyl)phosphinic chloride or 1,1'-dicarbonyldiimidazole before reaction with the hydrazine.

When $Z^1$ is not a group Z, it is, for example, an allylformyloxime group which can be converted to a carboxaldehydeoxime using tetrakis(triphenylphosphine)palladium (0) generally under an inert atmosphere such as nitrogen in the presence of triethylammonium formate, in a solvent such as ethanol for about 18 hours. The carboxaldehydeoxime can be converted to a carboxaldehydechloroxime by reacting with a chlorinating agent such as N-chlorosuccinimide in a solvent such as DMP. The carboxaldehydechloroxime can be converted to the desired group Z by reacting with an unsaturated compound such a vinylidene chloride, methyl propargyl ether, 3-phenyl-1-propyne, 2-pyridylacetylene, trifluoromethylacetylene or ethoxyacetylene generally in the presence of a base such a triethylamine, and a solvent such as dichloromethane. Alternatively, the carboxaldehydechloroxime can be converted to a group Z by reacting with ammonium hydroxide generally in a solvent such as ethanol for about 30 minutes and then acetic anhydride generally with heating to reflux for about 16 hours.

Compounds of formula III in which G is $OCH_2CF_3$ can be prepared by reacting a compound of formula III in which G is chlorine with 2,2,2-trifluoroethanol in the presence of a base such as lithium bis(trimethylsilyl)amide generally in a solvent such as DMF, preferably with cooling to about –20° C.–0° C. for a period of about 30 minutes.

The compound of formula V is prepared by reaction of a compound of formula VII:

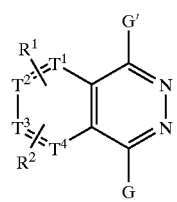

(VII)

where $T^1$, $T^2$, $T^3$, $T^4$, $R^1$, $R^2$ and G are as defined above, and G' is another suitable leaving group which may be the same as or different to G, with hydrazine, usually in the form of its monohydrate, generally in a solvent, such as ethanol and generally by refluxing for a suitable period such as 15 minutes to 2 hours.

As the compound of formula VII is asymmetrical, the substitution pattern about the fused benzene ring is not symmetrical. Consequently the reaction between this compound and hydrazine will usually give rise to a mixture of isomeric products depending on whether group G or G' is displaced first. Thus in addition to the required product of formula V, the isomeric compound wherein the $R^1$ and $R^2$ moieties are reversed or where the nitrogen atom in the fused pyridine ring is in its alternative location, will usually be obtained to some extent. For this reason it will generally be necessary to separate the resulting mixture of isomers by conventional methods such as chromatography.

The compound of formula VII can be used to prepare a compound of formula III in a single step by reacting with the appropriate hydrazoic acid, that is a compound of formula XIII:

$H_2NNHC(O)Z$      (XIII)

wherein Z is as defined above. This is generally carried out in the presence of a base, such as triethylamine, in a solvent such as xylene, at reflux under an inert atmosphere such as nitrogen.

The compound of formula VII can be prepared by reacting a compound of formula X:

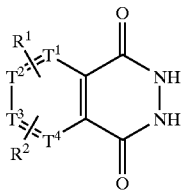 (X)

where $T^1$, $T^2$, $T^3$, $T^4$, $R^1$ and $R^2$ are as defined above, with a suitable reagent for introducing leaving groups G and $G^1$, for example where G and $G^1$ are both chlorine $POCl_3$ can be used generally with heating to reflux for about 16 hours.

The compound of formula X can be prepared by reacting a compound of formula XI with hydrazine hydrate ($H_2NNH_2.H_2O$):

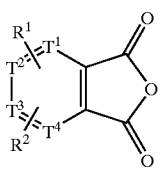 (XI)

where $T^1$, $T^2$, $T^3$, $T^4$, $R^1$ and $R^2$ are as defined above. The reaction is generally carried out in a protic solvent, such as 40% aqueous acetic acid, and in the presence of a buffering agent such as sodium acetate, generally with heating to reflux for about 16 hours to about 4 days.

The compound of formula XI can be prepared by reaction of a compound of formula XII:

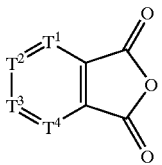 (XII)

wherein $T^1$, $T^2$, $T^3$ and $T^4$ are as defined above with suitable reagents to introduce the substituents $R^1$ and $R^2$ where necessary. For example, when $R^1$ is phenyloxy or pyridyloxy or a derivative thereof, the corresponding hydroxy compound can be used as a reagent. The compounds of formula XII are commercially available.

Alternatively, when $R^1$ is the same as L—Y—X in the compound of formula I, it can be introduced by displacing another group $R^1$ which can act as a leaving group, such as fluorine, in the reaction between the compounds of formulae III and IV.

In another procedure, the compounds according to the invention wherein L is O may be prepared by a process which comprises reacting a compound of formula VIII with a compound of formula IX:

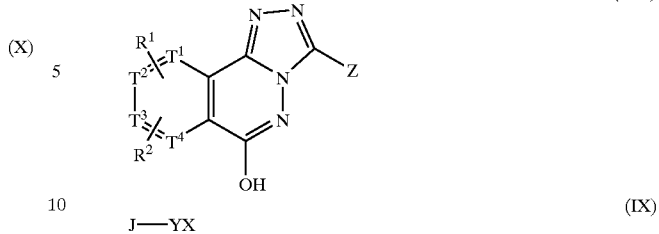

(VIII)

J—YX (IX)

wherein $T^1$, $T^2$, $T^3$, $T^4$, $R^1$, $R^2$, X, Y and Z are as defined above and J represents a suitable leaving group such as a halogen atom, typically chlorine. The reaction between compounds VIII and IX is conveniently effected by stirring the reactants in a suitable solvent, typically N,N-dimethylformamide, in the presence of a strong base such as sodium hydride.

The intermediates of formula VIII above may be conveniently prepared by reacting a compound of formula III as defined above with an alkaline hydroxide, e.g. sodium hydroxide. The reaction is conveniently effected in an inert solvent such as 1,4-dioxane, ideally at the reflux temperature of the solvent. A compound of formula III in which G is para-sulphonyltoluene can be made by reacting a compound of formula VIII with 4-toluenesulphonylchloride.

Alternatively, the intermediates of formula VIII (or the tautomeric 5-ones, which are equally suitable for reaction with compounds of formula IX) may be prepared by reacting a compound of formula VI with a compound of formula XIV:

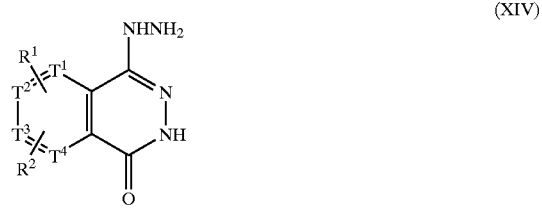 (XIV)

wherein $T^1$, $T^2$, $T^3$, $T^4$, $R^1$ and $R^2$ are as defined above, under the conditions described above for the reaction of compounds of formula V with compounds of formula VI.

Where they are not commercially available, the starting materials of formula IV, VI, VIII, IX and XIV may be prepared by methods analogous to those described in the accompanying Examples, or by standard methods known from the art.

It will be understood that any compound of formula I initially obtained from the above process may, where appropriate, subsequently be elaborated into a further compound of formula I by techniques known from the art. For example, a compound of formula I in which one of $T^1$, $T^2$, $T^3$ and $T^4$ represents N can be converted to the corresponding compound in which $T^1$, $T^2$, $T^3$ or $T^4$ represents $N^+$—$O^-$ by standard methods of oxidation, e.g. by means of m-chloroperoxybenzoic acid in an inert organic solvent at room temperature.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organtic Synthesis*, John Wiley & Sons, 1991. The protecting groups may be removed at a convenient subsequent stage using methods known from the art.

The compounds in accordance with this invention potently inhibit the binding of [$^3$H]-flumazenil to the benzodiazepine binding site of human GABA$_A$ receptors containing the α5 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1γ3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 M final concentration.

100 μl of cells.

Assays are incubated for 1 hour at 40° C., then filtered using either a Tomtec or Brandel cell harvester onto GFIB filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by nonlinear least squares regression analysis, from which the inhibition constant $K_i$ can be calculated for each test compound.

The compounds of the accompanying Examples were tested in the, above assay, and all were found to possess a $K_i$ value for displacement of [$^3$H]Ro 15–1788 from the α5 subunit of the human GABA$_A$ receptor of 100 nM or less, most were at 50 nM or less, many were at 10 nM or less and some were at 1 nM or less.

The compounds of the present invention have been shown to enhance cognition in the rat water maze test (Morris, Learning and Motivation, 1981, 12 239ff). Further details of methodology for demonstrating that the present compounds enhance cognition can be found in WO-A-9625948.

The following Examples illustrate the present invention:

EXAMPLE 1

3-(5-Methylisoxazol-3-yl)-5-(2-pyridylmethyloxy)-1,2,3a,4,6-pentaaza-cyclopenta[a]naphthalene a) 6,7-Dihydro-pyrido[2,3-d]pyridazine-5,8-dione Hydrazine hydrate (13.09 g, 0.261 mol) was added to a stirred solution of pyridine-2,3-dicarboxylic anhydride (30.0 g, 0.201 mol) and sodium acetate (21.45 g, 0.261 mol) in 40% acetic acid/water (400 ml). The reaction was heated at reflux for 3 days under nitrogen. The yellow precipitate was filtered off and washed successively with water (4×200 ml), hexane (3×150 ml) and diethyl ether (3×150 ml) to give the title-compound (25.0 g, 76%), $^1$H NMR (250 MHz, d$^6$-DMSO) δ 7.90 (1H, q, J=4.5Hz, Ar—H), 8.51 (1H, d, J=4.5Hz, Ar—H), 9.13 (1H, d, J=4.6Hz, Ar—H), 11.65 (2H, br s, 2 of NH); MS (ES$^+$) m/e 164 [MH]$^+$.

b) 5,8-Dichloro-pyrido[2,3-d]pyridazine

The preceding compound (25.0 g, 0.185 mol) was dissolved in phosphorus oxychloride (260 ml) and heated at reflux for 4 h under nitrogen. The solvent was removed in vuacuo and the resulting brown solid was taken up in dichloromethane (300 ml) and water (100 ml) and sodium hydrogen carbonate added until the mixture was neutral. The mixture was filtered and the organic layer was separated. The aqueous layer was extracted with dichloromethane (2×200 ml) and the combined organic layers were dried (MgSO$_4$) and evaporated in vacuo. The brick-red coloured solid was dissolved in hot dichloromethane, filtered and triturated with diethyl ether to give the title-compound (15.2 g, 50%), $^1$H NMR (250 MHz, CDCl$_3$) δ 7.25 (1H, m, Ar—H), 7.87 (1H, q, J=4.6Hz, Ar—H), 8.03 (1H, d, J=4.6Hz, Ar—H).

c) 5-Methylisoxazole-3-carboxylic Acid Hydrazide

To a solution of ethyl 5-methylisoxazole-3-carboxylate (3.0 g, 19 mmol) in methanol (30 ml) at 0° C. under nitrogen was added hydrazine hydrate (3.04 g, 95 mmol) over 0.3 h. The reaction was stirred at 0° C. for 0.25 h and at RT for 1 h. The white precipitate was filtered off and washed with methanol to give the title-compound (0.78 g, 29%) as a white solid, $^1$H NMR (250 MHz, CDCl$_3$) δ 2.41 (3H, d, J=0.8 Hz, CH$_3$), 4.07 (2H, br s, NH$_2$), 6.44 (1H, q, J=0.8 Hz, Ar—H), 7.99 (1H, br s, N—H); MS (ES$^+$) m/e 142 [MH]$^+$.

d) 5-Chloro-3-(5-methylisoxazol-3-yl)-1,2,3a,4,6-pentaaza-cyclopenta[a]naphthalene and 5-Chloro-3-(5-methylisoxazol-3-yl)-1,2,3a,4,9-pentaazat-cyclopenta[a]naphthalene.

To a solution of 5,8-dichloro-pyrido[2,3-d]pyridazine (2.21 g, 11 mmol) and 5-methylisoxazole-3-carboxylic acid hydrazide (1.57 g, 11 mmol) in xylene (70 ml) was added triethylamine (1.55 ml, 11 mmol). The reaction was heated at reflux under nitrogen for 16 h. The solvent was evaporated in vacuo and the residue taken up in dichloromethane (150 ml), washed with water (3×75 ml), dried (MgSO$_4$) and evaporated in vacuo. The crude product was purified by chromatography on silica gel, eluting with 4% methanol/dichloromethane. The two isomers were separated by chromatography on alumina (Grade III), eluting with 0.5% ethanol/dichloromethane to give:

5-Chloro-3-(5-methylisoxazol-3-yl)-1,2,3a,4,9-pentaaza-cyclopenta[a]naphthalene (more polar isomer)(0.25 g, 8%): $^1$H NMR (360 MHz, d$^6$-DMSO) δ 3.31 (3H, s, CH$_3$), 7.01 (1H, d, J=0.8 Hz, Ar—H), 8.08 (1H, q, J=4.5 Hz, Ar—H), 8.75 (1H, d, J=4.5 Hz, Ar—H) 9.33 (1H, q, J=4.7 Hz, Ar—H).

5-Chloro-3-(5-methylisoxazol-3-yl)-1,2,3a,4,9-pentaaza-cyclopenta[a]naphthalene (less polar isomer) (0.4 g, 13%): $^1$H NMR (360 MHz, d$^6$-DMSO) δ 3.31 (3H, s, CH$_3$), 7.01 (1H, d, J=0.7 Hz, Ar—H), 8.15 (1H, q, J=4.6 Hz, Ar—H), 9.04 (1H, dd, J=8.2 Hz and 1.6 Hz, Ar—H), 9.27 (1H, dd, J=4.6 Hz and 1.5 Hz, Ar—H).

e) 3-(5-Methylisoxazol-3-yl)-5-(2-pyridylmethyloxy)-1,2,3a,4,6-pentaaza-cyclopenta[a]naphthalene Sodium hydride (63 mg of a 60% dispersion in oil, 1.57 mmol) was added to a stirred solution of 2-pyridyl carbinol (87 mg, 0.84 mmol) in DMF (15 ml) at room temperature under nitrogen and the mixture stirred for 0.25 h. After this time the less polar chloride (225 mg, 0.79 mmol) was added and the mixture stirred for 2 h. The solvent was evaporated in vacuo and the residue dissolved in dichloromethane, washed with water (x2), dried (MgSO$_4$) and evaporated in vacuo. Flash chromatography of the residue on silica gel, eluting with 4% methanol/dichloromethane, gave the title-product (100 mg, 35%), $^1$H NMR (360 MHz, CDCl$_3$) δ 2.59 (3H, d, J=0.7 Hz, CH$_3$), 5.88 (2H, s, CH$_2$), 6.81 (1H, s, Ar—H), 7.27 (1H, m, Ar—H), 7.71–7.77 (2H, m, 2 of Ar—H), 7.89 (1H, q, J=4.7 Hz, Ar—H), 8.70 (1H, d, J=4.7 Hz, Ar—H), 9.00 (1H, q, J=8.1 Hz, Ar—H), 9.18 (1H, q, J=4.5 Hz, Ar—H); MS (ES$^+$) m/e 360 [MH]$^+$; Anal. Found. C, 59.36; H, 3.36; N, 26.80. C$_{18}$H$_{13}$N$_7$O$_2$. 0.1 (CH$_2$Cl$_2$) requires C, 59.10; H, 3.61; N, 26.65%.

EXAMPLE 2

3-(5-Methylisoxazol-3-yl)-5-(2-pyridylmethyloxy)-1,2,3a,4,9-pentaaza-cyclopenta[a]naphthalene The title-compound was prepared from 5-chloro-3-(5-methylisoxazol-3-yl)-1,2,3a,4,9-pentaaza-cyclopenta[a]naphthalene according to the procedure given in Example 1, part e. $^1$H NMR (360 MHz, CDCl$_3$) δ 2.59 (3H, s, Ar—H), 5.78 (2H, s, CH$_2$), 6.85 (1H, d, J=0.8 Hz, Ar—H), 7.29 (1H, m, Ar—H), 7.74–7.79 (3H, m, 3 of Ar—H), 8.62 (1H, d, J=8.0 Hz, Ar—H), 8.70 (1H, d, J=4.6 Hz, Ar—H), 9.23 (1H, q, J=4.6 Hz, Ar—H); MS (ES$^+$) m/e 360 [MH]$^+$. Anal. Found. C, 60.02; H, 3.31; N, 27.00. C$_{18}$H$_{13}$N$_7$O$_2$ requires C, 60.16; H, 3.65; N, 27.28%.

EXAMPLE 3

3-(5-Methylisoxazol-3-yl)-5-(2-pyridylmethyloxy)-1,2,3a,4,7-pentaaza-cyclopenta[a]naphthalene and 3-(5-Methylisoxazol-3-yl)-5-(2-pyridylmethyloxy)-1,2,3a,4,8-pentaaza-cyclopenta[a]naphthalene The title-compounds were prepared as described in Example 1, parts a–e, using pyridine-3,4 dicarboxylic anhydride instead of pyridine-2,3-dicarboxylic anhydride in part a. The isomers were separated in part e by HPLC:

3-(5-Methylisoxazol-3-yl)-5-(2-pyridylmethyloxy)-1,2,3a,4,7-pentaaza-cyclopenta[a]naphthalene: 1H NMR (500 MHz, CDCl$_3$) δ 2.73 (3H, s, CH$_3$), 5.94 (2H, s, CH$_2$), 6.97 (1H, s, Ar—H), 7.47 (1H, t, J=6.0 Hz, Ar—H), 7.90–7.96 (2H, m, 2 of Ar—H), 8.62 (1H, d, J=5.3 Hz, Ar—H), 8.82 (1H, d, J=4.6 Hz, Ar—H), 9.27 (1H, d, J=5.3 Hz, Ar—H), 9.75 (1H, s, Ar—H); MS (ES$^+$) m/e 360 [MH]$^+$.

3-(5-Methylisoxazol-3-yl)-5-(2-pyridylmethyloxy)-1,2,3a,4,8-pentaaza-cyclopenta[a]naphthalene: $^1$H NMR (360 MHz, CDCl$_3$) δ 2.60 (3H, d, J=0.7 Hz, CH$_3$), 5.78 (2H, s, CH$_2$), 6.82 (1H, s, Ar—H), 7.31 (1H, m, 2 of Ar—H), 7.74–7.78 (2H, m, 2 of Ar—H), 8.08 (1H, d, J=4.5 Hz, Ar—H), 8.70 (1H, d, J=4.5 Hz, Ar—H), 9.08 (1H, d, J=5.3 Hz), 10.03 (1H, s, Ar—H); MS (ES$^+$) m/e 360 [MH]$^+$.

EXAMPLE 4

3-(5-Methylisoxazol-3-yl)-5-(2-methyl-1,2,4-triazol-3-ylmethyloxy)-1,2,3a,4,6-pentaaza-cyclopenta[a]naphthalene A solution of 5-chloro-3-(5-methylisoxazol-3-yl)-1,2,3a,4,6-pentaaza-cyclopenta[a]naphthalene (100 mg, 0.35 mmol) in N,N-dimethyl formamide (7 ml) was added to a solution of 2-methyl-1,2,4-triazole-3-methanol (43 mg, 0.38 mmol) (prepared using the conditions of Itoh and Okongi, EP-A-421210) under nitrogen, and the mixture cooled to −78° C. Lithium bis(trimethylsilyl)amide (0.42 ml, 1.0 M in tetrahydrofuran, 0.42 mmol) was added, and the reaction stirred at −78° C. for 2 h, then allowed to warm to room temperature and stirred for 3 h. The solvents were evaporated by azeotroping with xylene and the residue pre-absorbed onto silica (1 g) from methanol/dichloromethane. Flash chromatography on a silica bond elute cartridge (10 g) eluting with a 0%→5% methanol/dichloromethane gradient, followed by recrystallisation (dichloromethane/ethyl acetate) gave the title-product (52 mg, 41%), mp 255–257° C.; $^1$H NMR (360 MHz, CDCl$_3$) δ 9.16 (1H, dd, J=4.4 Hz and 1.7 Hz, Ar—H), 9.01 (1H, dd, J=8.2 Hz and 1.7 Hz, Ar—H), 7.92 (1H, m, Ar—H), 7.90 (1H, s, Ar—H), 6.93 (1H, s, Ar—H), 5.88 (2H, s, CH$_2$), 4.12 (3H, s, CH3), 2.60 (3H, s, CH$_3$); MS (ES$^+$) m/e 364 [MH]$^+$.

EXAMPLE 5

3-(5-Ethoxyisoxazol-3-yl)-5-(1-methyl-1,2,4-triazol-3-ylmethyloxy)-1,2,3a,4,6-pentaaza-cyclonenta[a]naphthalene a) 4-Chloro-1-hydrazino-2,3,5-azanaphthalene and 1-Chloro-4-hydrazino-2,3,5-azanaphthalene To a solution of 5,8-dichloropyrido[2,3-d]pyridazine (21.5 g, 108 mmol) (prepared as described in Example 1, part b) in ethanol (600 ml) was added hydrazine hydrate (32.4 g, 65 mmol). The reaction was stirred at room temperature for 18 h and the precipitate filtered off and washed with diethyl ether to give the title compounds as a brick redsolid (21.0 g, 100%), $^1$H NMR (250 MHz, d$^6$-DMSO) δ 9.16 (1H, m, Ar—H), 8.45 (1H, m, Ar—H), 8.03 (1H, m, Ar—H), 4.69 (2H, br s, NH$_2$). The regioisomers were separated by chromatography.

b) 5-Chloro-3-dichloromethyl-1,2,3a,4,6-pentaaza-cyclopenta[a]naphthalene

To the preceding hydrazine (54 g, 277 mmol) in toluene (400 ml) was added dichloroacetic acid (150 ml) and the reagents heated under Dean-Stark conditions for 1.5 h. On cooling, saturated potassium carbonate solution (aq) (200 ml) was added. The emulsion formed was filtered through celite, and the filtrate evaporated in vacuo. The residue was taken in dichloromethane and washed with water (x2). The organic phase was dried (MgSO$_4$) and evaporated in vacuo.

The required isomer was separated by chromatography on silica gel, eluting with 20%→100% ethyl acetate/hexane to give the title-compound (4.69 g, 6%) (less polar isomer), $^1$H NMR (250 MHz, CDCl$_3$) δ 7.32 (1H, s, C—H), 7.99 (1H, m, Ar—H), 9.05 (1H, dd, J=1.6 Hz and 8.1 Hz, Ar—H) 9.26 (1H, dd, J=1.7 Hz and 4.6 Hz, Ar—H).

c) 3-Dichloromethyl-5-(2,2,2-trifluoroethyloxy)-1,2,3a,4,6-pentaaza-cyclopenta[a]naphthalene A solution of the preceding chloride (4.69 g, 16 mmol) in N,N-dimethylformamide (40 ml) was added to a solution of 2,2,2-trifluoroethanol (1.3 ml, 17.8 mmol) in tetrahydrofuran (30 ml), under nitrogen, and the mixture cooled to −78° C. Lithium bis(trimethylsilyl)amide (19.5 ml, 1.0M in tetrahydrofuran, 19.5 mmol) was added, and the mixture stirred at −78° C. for 0.5 h, then at room temperature for 2 h. The solvent was evaporated in vacuo by azeotroping with xylene, and the residue partitioned between dichloromethane and water. The aqueous phase was separated and extracted with dichloromethane (x3). The combined organic phases were dried (MgSO$_4$) and the solvent in vacuo. Flash chromatography of the residue on silica gel, eluting with 1%→3% methanol/dichloromethane gave the title-compound (2.5 g, 44%), $^1$H NMR (250 MHz, CDCl$_3$) δ 9.24 (1H, dd, J=4.6 Hz and 1.6 Hz, Ar—H), 8.99 (1H, dd, J=8.2 Hz and 1.7 Hz, Ar—H) 7.95 (1H, m, Ar—H), 7.28 (1H, s, C—H) 5.08 (2H, q, J=8.0 Hz, CH$_2$); MS (ES$^+$) m/e 352 [MH]$^+$.

d) 3-Carboxamidoxime-5-(2,2,2)-trifluoroethyloxy-1,2,3a,4,6-pentaza-cyclopenta[a]naphthalene To the preceding product (2.5 g, 7 mmol) in formic acid (213 ml) and water (36 ml), was added hydroxylamine hydrochloride (0.987 g, 14 mmol) and the reagents heated at 110° C. for 20 h. On cooling, the solvent was evaporated in vacuo and the residue triturated with water, filtered and washed successively with water and diethyl ether to give the title-product (1.1 g, 50%), $^1$H NMR (250 MHz, d$^6$-DMSO) δ 12.51 and 67 12.30 (1H, 2×S, C—H E and Z), 9.18 (1H, dd, J=4.5 Hz and 1.4 Hz, Ar—H), 8.93 (1H, dd, J=8.2 Hz and 1.6 Hz, Ar—H), 8.60 and 8.14 (1H, s, OH E and Z), 8.10 (1H, m, Ar—H), 5.29 (2H, q, J=8.8 Hz, CH$_2$); MS (ES$^+$) m/e 313 [MH]$^+$.

e) 3-Carboxamidochloroxime-5-(2,2,2)-trifluoroethyloxy-1,2,3a,4,6-pentaaza-cyclopenta[a]naphthalene To the preceding product (1.1 g, 35 mmol) in N,N-dimethylformamide (60 ml) was added N-chlorosuccinimide (0.471 g, 35 mmol) and the mixture heated briefly until the reagents were in solution. The mixture was allowed to cool, and poured into ice/water (100 ml). The precipitate was filtered off, washed with water and ethanol and dried to give the title-compound (0.696 g, 57%), $^1$H NMR (250 MHz, d$^6$-DMSO) δ 13.33 (1H, s, OH), 9.22 (1H, dd, J=4.5 Hz and 1.5 Hz, Ar—H), 8.98 (1H, dd, J=8.2 Hz and 1.5 Hz, Ar—H), δ 8.11 (1H, m, Ar—H), 5.19 (2H, q, J=8.7 Hz, CH$_2$).

f) 3-(5-Ethoxyisoxazol-3-yl)-5-(2,2,2-trifluoroethyloxy)-1,2,3a,4,6-pentaaza-cyclopenta[a]naphthalene To the preceding product (692 mg, 2 mmol) in dichloromethane at room temperature under nitrogen was added ethoxyacetylene (40% solution in hexanes, 1.05 g, 6 mmol). A solution of triethylamine (0.28 ml, 2 mmol) in dichloromethane (30 ml) was then added dropwise over 1 h. The mixture was stirred for 1 h, the solvent evaporated and the residue triturated with water and filtered. The solid was washed with water, hexane, and diethyl ether. Flash chromatography on silica gel, eluting with 2%→4% methanol/dichloromethane (gradient elution), gave the title-compound (580 mg, 76%), $^1$H NMR (250 MHz, CDCl$_3$) δ 9.22 (1H, dd, J=4.6 Hz and 1.7 Hz, Ar—H(9.02 (1H, dd, J=8.2 Hz and 1.7 Hz, Ar—H), 7.94 (1H, m, Ar—H), 6.06 (1H, s, Ar—H), 5.09 (2H, q, J=8.0 Hz, CH$_2$), 4.41 (2H, q, J=7.1 Hz, CH$_2$), 1.55 (3H, t, J=7.1 Hz, CH$_3$).

g) 3-(5-Ethoxyisoxazol-3-yl)-5-(1-methyl-1,2,4-triazol-3-ylmethyloxy)-1,2,3a,4,6-pentaaza-cyclopenta[a]naphthalene The title-compound was prepared from the preceding product (145 mg, 0.38 mmol) and 1-methyl 1,2,4-triazole-3-methanol (prepared using the conditions of Itoh and Okongi, EP-A-421210) (47 mg, 0.42 mmol) following the procedure described in Example 4 part b, $^1$H NMR (360 MHz, CDCl$_3$) δ 9.15 (1H, dd, J=4.5 Hz and 1.7 Hz, Ar—H), 8.99 (1H, dd, J=8.0 Hz and 1.7 Hz, Ar—H), 8.04 (1H, s, Ar—H) 7.87 (1H, m, Ar—H), 6.25 (1H, s, Ar—H), 5.79 (2H, s, CH$_2$), 4.43 (2H, q, J=7.1 Hz, CH$_2$), 3.94 (3H, s, CH$_3$), 1.54 (2H, t, J=7.1 Hz, CH$_3$); MS (ES$^+$) m/e 394 [MH]$^+$; Anal. Found. C, 51.34; H, 3.62; N, 31.91. C$_{17}$H$_{15}$N$_9$O$_2$.0.1H$_2$O requires C, 51.67; H, 3.88; N, 31.90%.

EXAMPLE 6

3-(5-Methylisoxazol-3-yl)-5-(1-methyl-1,2,3-triazol-4-ylmethyloxy)-1,2,3a,4,7-pentaaza-cyclopenta[a]naphthalene a) 5-Methyl-3-isoxazolecarboxylic Acid 2-(Pyrido[3,4-d]pyridazin-4(3H)-one-1-yl)hydrazide 1-Hydrazinopyrido[3,4-d]pyridazin-3(4H)-one [prepared by the method of K. Kormendy, T. Kovacs, F. Ruff and I. Kovesdi, Acta Chim. Hung., 1983, 112(4), 487] (1.72 g, 9.7 mmol), triethylamine (1.36 ml, 9.7 mmol), 5-methylisoxazole-3-carboxylic acid (1.23 g, 9.7 mmol) and bis(2-oxo-3-oxazolidinyl)phosphinic acid (2.48 g, 9.7 mmol) in 1,2-dichloroethane (60 ml) were heated at reflux under nitrogen for 18 h. The mixture was allowed to cool and diluted with water (20 ml). The precipitate was filtered off and washed successively with water (2×50 ml) and diethyl ether (2×50 ml) to give the title compound (2.2 g, 79%), $^1$H NMR (400 MHz, d$^6$ DMSO) δ 2.50 (3H, s, Ar—CH$_3$), 6.62 (1H, s, Ar—H), 8.04 (1H, d, J=5.5 Hz, Ar—H), 9.10 (1H, d, J=5.5 Hz, Ar—H), 9.11 (1H, s, Ar—H), 9.45 (1H, s, NH), 10.62 (1H, s, NH), 12.08 (1H, s, NH).

b) 3-(5-Methylisoxazol-3-yl)-1,2,3a,4,7-pentaazacyclopenta[a]naphthalen-5(4H)-one The preceding compound (2.0 g, 7.0 mmol) intrifluoroacetic acid (40 ml) was heated at reflux under N$_2$ for 3.5 days. The solvent was removed in vacuo and the residue washed with saturated sodium hydrogen carbonate solution (30 ml). The solid was filtered and washed successively with water (60 ml) and diethyl ether (50 ml). The title compound was isolated as a yellow solid (770 mg, 41%), $^1$H NMR (400 MHz, d$^6$ DMSO) δ 2.58 (3H, s, Ar—CH$_3$), 7.03 (1H, s, Ar—H), 8.41 (1H, d, J=5.3 Hz, Ar—H), 9.13 (1H, d, J=5.3 Hz, Ar—H), 9.44 (1H, s, Ar—H).

c) 3-(5-Methylisoxazol-3-yl)-5-(1-methyl-1,2,3-triazol-4-ylmethyloxy)-1,2,3a,4,7-pentaaza-cyclopenta[a]naphthalene Sodium hydride (42 mg of a 60% dispersion on oil, 1.1 mmol) was added to a stirred solution of 3-(5-methylisoxazol-3-yl)-1,2,3a,4,7-pentaazacyclopenta[a]naphthalen-5(4H)-one (200 mg, 0.75 mmol) in DMF (6 ml) at room temperature under nitrogen, and the mixture was heated at 60° C. for 0.5 h. The reaction mixture was allowed to cool to room temperature, treated with 4-chloromethyl-1-methyl-1,2,3-triazole (108 mg, 0.82 mmol) and heated at 60° C. for 1.5 h. On cooling to room, water was added. The mixture was extracted with ethyl acetate, the organics separated, dried (MgSO$_4$), and evaporated in vacuo. The residue was recrystallised from methanol to afford the title product as a white solid (39 mg, 14%), $^1$H NMR (360 MHz, d$^6$ DMSO) δ 2.60 (3H, s, Ar—CH$_3$), 4.08 (3H, s, N—CH$_3$), 5.73 (2H, s, OCH$_2$), 7.21 (1H, d, J=0.8 Hz, Ar—H), 8.45 (2H, m, Ar—H), 9.15 (1H, d, J=5.3 Hz, Ar—H)), 9.41 (1H, s, Ar—H); MS (ES$^+$) m/e 364 [MH]$^+$.

EXAMPLE 7

3-(5-Methylisoxazol-3-yl)-5-(1-methyl-1,2,4-triazol-3-ylmethyloxy)-1,2,3a,4,7-pentaaza-cyclopenta[a]naphthalene The title compound was prepared from 3-(5-methylisoxazol-3-yl)-1,2,3a,4,7-pentaazacyclopenta[a]naphthalen-5(4H)-one according to the procedure given in Example 6, part c. $^1$H NMR (400 MHz, d$^6$ DMSO) δ 2.61 (3H, s, Ar—CH$_3$), 3.91 (3H, s, N—CH$_3$), 5.65 (2H, s, OCH$_2$), 7.31 (1H, s, Ar—H), 8.45 (1H, d, J=5.3 Hz, Ar—H), 8.57 (1H, s, Ar—H), 9.15 (1H, d, J=5.2 Hz, Ar—H), 9.38 (1H, s, Ar—H); MS (ES$^+$) m/e 364 [MH]$^+$.

EXAMPLE 8

3-(5-Methylisoxazol-3-yl)-5-(3-trifluoromethyl-2-pyridylmethyloxy)-1,2,3a,4,7-pentaaza-cyclopenta[a]naphthalene The title compound was prepared from 3-(5-methylisoxazol-3-yl)-1,2,3a,4,7-pentaazacyclopenta[a]naphthalen-5(4H)-one according to the procedure given in Example 6, part c. $^1$H NMR (400 MHz, d$^6$ DMSO) δ 2.56 (3H, s, Ar—CH$_3$), 5.94 (2H, s, OCH$_2$), 6.89 (1H, s, Ar—H), 7.70 (1H, t, J=6.3 Hz, Ar—H), 8.35 (1H, d, J=8.0 Hz, Ar—H), 8.47 (1H, d, J=5.3 Hz, Ar—H), 8.90 (1H, s, Ar—H), 9.18 (1H, d, J=5.2 Hz, Ar—H), 9.43 (1H, s, Ar—H).

EXAMPLE 9

3-(5-Methylisoxazol-3-yl)-5-(1-methyl-1,2,3-triazol-4-ylmethyloxy)-7-oxide-1,2,3a,4,7-pentaaza-cyclopenta[a]naphthalene 3-(5-Methylisoxazol-3-yl)-5-(1-methyl-1,2,3-triazol-4-ylmethyloxy)1,2,3a,4,7-pentaaza-cyclopenta[a]naphthalene (70 mg, 0.2 mmol) in dichloromethane under N$_2$ was treated with 3-chloroperoxybenzoic acid (66 mg, 0.4 mmol) and heated at reflux for 5 h. On cooling the mixture was filtered, the mother liquors diluted with dichloromethane and washed with saturated aqueous sodium hydrogen carbonate solution and water. The organics were separated, dried (MgSO$_4$) and concentrated in vacuo. The residue was recrystallised from methanol to afford the title compound (4 mg, 5%), $^1$H NMR (360 MHz d$^6$ DMSO) δ 2.60 (3H, s, Ar—CH$_3$), 4.07 (3H, s, N—CH$_3$), 5.69 (2H, s, OCH$_2$), 7.18 (1H, s, Ar—H), 8.45 (2H, m, Ar—H), 8.69 (1H, m, Ar—H), 8.76 (1H, s, Ar—H); MS (ES$^+$) m/e 380 [MH]$^+$.

What is claimed is:
1. A compound of the formula I:

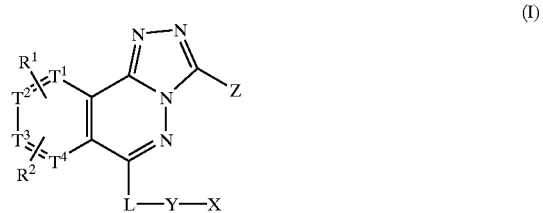

wherein:
R$^1$ is hydrogen, halogen or CN or a group CF$_3$, OCF$_3$, C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;

R$^2$ is hydrogen, halogen or CN or a group CF$_3$, OCF$_3$, C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy each of which groups is unsubstituted or substituted with one or two halogen atoms;

L is O, S or NR$^n$ where R$^n$ is H, C$_{1-6}$alkyl or C$_{3-6}$cycloalkyl;

one of T$^1$, T$^2$, T$^3$ and T$^4$ is nitrogen or N$^+$—O— and the others are CH;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by R$^x$ and/or R$^y$ and/or R$^z$, where R$^x$ is halogen, R$^3$, OR$^3$, OCOR$^3$, NR$^4$R$^5$, NR$^4$COR$^5$, tri(C$_{1-6}$alkyl)silylC$_{1-6}$alkoxyC$_{1-4}$alkyl, CN or R$^9$, R$^y$ is halogen, R$^3$, OR$^3$, OCOR$^3$, NR$^4$R$^5$, NR$^4$COR$^5$ or CN and R$^z$ is R$^3$, OR$^3$ or OCOR$^3$, where R$^3$ is C$_{1-6}$alkyl, C$_{2-6}$alkenyl, C$_{2-6}$alkynyl, C$_{3-6}$cycloalkyl, hydroxyC$_{1-6}$alkyl and R$^3$ is optionally mono, di- or tri-fluorinated, R$^4$ and R$^5$ are each independently hydrogen, C$_{1-6}$alkyl, C$_{2-6}$alkenyl, C$_{2-6}$alkynyl, C$_{3-6}$cycloalkyl or CF$_3$ or R$^4$ and R$^5$, together with the nitrogen atom to which they are attached, form a 4–7 membered heteroaliphatic ring containing the nitrogen atom as the sole heteroatom, and R$^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and R$^9$ is optionally substituted by one, two or three substituents independently chosen from halogen atoms and C$_{1-4}$alkyl, C$_{2-4}$alkenyl, C$_{2-4}$alkynyl, C$_{1-4}$alkoxy, C$_{2-4}$alkenyloxy and C$_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a C$_{1-4}$alkyl group; or X is phenyl optionally substituted by one, two or three groups independently selected from halogen, cyano, C$_{1-6}$alkyl, C$_{2-6}$alkenyl, C$_{2-6}$alkynyl and C$_{3-6}$cycloalkyl;

Y is optionally branched $C_{2-4}$alkylene or $C_{1-4}$alkylidene optionally substituted by an oxo group or Y is a group $(CH_2)_jO$ wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

2. A compound according to claim 1 or a pharmaceutically acceptable salt thereof wherein one of $T^1$, $T^2$, $T^3$ and $T^4$ is nitrogen and the others are CH.

3. A compound according to claim 1 or a pharmaceutically acceptable salt thereof wherein $R^1$ and $R^2$ are hydrogen;

L is O;

X is pyridine or triazole and is unsubstituted or substituted by $C_{1-6}$alkyl or $CF_3$;

Y is $CH_2$; and

Z is isoxazole which is unsubstituted or substituted by $C_{1-6}$alkyl or $C_{1-6}$alkoxy.

4. A compound according to claim 1 or a pharmaceutically acceptable salt thereof wherein X is a 1,2,3- or 1,2,4-triazole which is substituted by methyl or ethyl.

5. A compound according to claim 1 or a pharmaceutically acceptable salt thereof wherein X is pyridine and is unsubstituted or substituted by $C_{1-6}$alkyl or $CF_3$.

6. A compound according to claim 3 selected from:

3-(5-methylisoxazol-3-yl)-5-(2-pyridylmethyloxy)-1,2,3a,4,6-pentaaza-cyclopenta[a]naphthalene;

3-(5-methylisoxazol-3-yl)-5-(2-pyridylmethyloxy)-1,2,3a,4,9-pentaaza-cyclopenta[a]naphthalene;

3-(5-methylisoxazol-3-yl)-5-(2-pyridylmethyloxy)-1,2,3a,4,7-pentaaza-cyclopenta[a]naphthalene;

3-(5-methylisoxazol3-yl)-5-(2-pyridylmethyloxy)-1,2,3a,4,8-pentaaza-cyclopenta[a]naphthalene;

3-(5-methylisoxazol-3-yl)-5-(2-methyl-1,2,4-triazol-3-ylmethyloxy)-1,2,3a,4,6-pentaaza-cyclopenta[a]naphthalene;

3-(5-ethoxylsoxazol-3-yl)-5-(1-methyl-1,2,4-triazol-3-ylmethyloxy)-1,2,3a,4,6-pentaaza-cyclopenta[a]naphthalene;

3-isoxazol-3-yl-5-(2-methyl-1,2,4-triazol-3-ylmethoxy)-1,2,3a,4,6-pentaaza-cyclopenta[a]naphthalene;

3-isoxazol-3-yl-5-(1-methyl-1,2,4-triazol-3-ylmethoxy)-1,2,3a,4,6-pentaaza-cyclopenta[a]naphthalene;

3-(5-methylisoxazol-3-yl)-5-(1-methyl-1,2,4-triazol-3-ylmethoxy)-1,2,3a,4,6-pentaaza-cyclopenta[a]naphthalene;

3-(5-methylisoxazol-3-yl)-5-(1-methyl-1,2,3-triazol-4-ylmethoxy)-1,2,3a,4,6-pentaaza-cyclopenta[a]naphthalene;

3-(5-methylisoxazol-3-yl)-5-(3-methyl-1,2,3-triazol-4-ylmethoxy)-1,2,3a,4,6-pentaaza-cyclopenta[a]naphthalene;

3-(5-methylisoxazol-3-yl)-5-(2-ethyl-1,2,4-triazol-3-ylmethoxy)-1,2,3a,4,6-pentaaza-cyclopenta[a]naphthalene;

3-(5-ethoxysoxazol-3-yl)-5-(1-methyl-1,2,3-triazol-4-ylmethoxy)-1,2,3a,4,6-pentaaza-cyclopenta[a]naphthalene;

3-(5-ethoxylsoxazol-3-yl)-5-(3-methyl-1,2,3-triazol-4-ylmethoxy)-1,2,3a,4,6-pentaaza-cyclopenta[a]naphthalene;

3-(5-ethoxylsoxazol-3-yl)-5-(2-ethyl-1,2,4-triazol-3-ylmethoxy)-1,2,3a,4,6-pentaaza-cyclopenta[a]naphthalene;

3-(5-methylisoxazol-3-yl)-5-(2-pyridylmethyloxy)-1,2,3a,4,7-pentaaza-cyclopenta[a]naphthalene;

3-(5-methylisoxazol-3-yl)-5-(1-methyl-1,2,3-triazol-4-ylmethyloxy)-1,2,3a,4,7-pentaaza-cyclopenta[a]naphthalene;

3-(5-methylisoxazol-3-yl)-5-(1-methyl-1,2,4-triazol-3-ylmethyloxy)-1,2,3a,4,7-pentaaza-cyclopenta[a]naphthalene;

3-(5-methylisoxazol-3-yl)-5-(3-trifluoromethyl-2-pyridylmethyloxy)-1,2,3a,4,7-pentaaza-cyclopenta[a]naphthalene;

3-(5-methylisoxazol-3-yl)-5-(1-methyl-1,2,3-triazol-4-ylmethyloxy)-7-oxide-1,2,3a,4,7-pentaaza-cyclopenta[a]naphthalene;

and pharmaceutically acceptable salts thereof.

7. A compound according to claim 1 or a pharmaceutically acceptable salt thereof which is binding selective for the $GABA_A$ $\alpha 5$ subunit relative to the $\alpha_1$, $\alpha_2$ and $\alpha^3$ subunits.

8. A compound according to claim 1 or a pharmaceutically acceptable salt thereof which is functionally selective for the $GABA_A$ $\alpha 5$ subunit as a partial or full inverse agonist and is an antagonist at the $\alpha_1$, $\alpha_2$ and $\alpha_3$ subunits.

9. A pharmaceutical composition comprising one or more compounds according to claim 1 or pharmaceutically acceptable salts thereof and a pharmaceutically acceptable carrier.

10. A method of treatment of a subject suffering from a cognition deficit which comprises administering to that subject an effective amount of a compound according to claim 1 or a pharmaceutically acceptable salt thereof.

* * * * *